United States Patent [19]

Brown et al.

[11] Patent Number: 5,837,872

[45] Date of Patent: Nov. 17, 1998

[54] PROCESS FOR PREPARATION OF N-ACYL-AMINODIACIDS

[75] Inventors: David M. Brown, Charlotte; Mohammad A. Khadim, Huntersville; Narayan D. Sadanani, Charlotte; April Yeager, Stanley, all of N.C.

[73] Assignee: Hoechst Celanese Corporation, Somerville, N.J.

[21] Appl. No.: 554,946

[22] Filed: Nov. 13, 1995

[51] Int. Cl.[6] .................................................. C07C 227/18
[52] U.S. Cl. ............................ 562/571; 562/573; 554/63
[58] Field of Search .............................. 554/63; 562/571, 562/573

[56] References Cited

U.S. PATENT DOCUMENTS

| 3,758,525 | 9/1973 | Yashida et al. | 554/63 |
| 3,927,047 | 12/1975 | Ichikawa et al. | 554/63 |

FOREIGN PATENT DOCUMENTS

| 2015075 | 11/1977 | Germany | 103/48 |
| 9424997 | 11/1994 | WIPO | 7/32 |

*Primary Examiner*—James H. Reamer
*Attorney, Agent, or Firm*—Scott E. Hanf

[57] ABSTRACT

This invention relates to an improved process for preparing selected N-acyl-aminodiacids such as lauroyl glutamic acid.

6 Claims, No Drawings

PROCESS FOR PREPARATION OF N-ACYL-AMINODIACIDS

FIELD OF THE INVENTION

This invention relates to an improved process for the preparation of N-acyl-aminodiacids.

BACKGROUND OF THE INVENTION

A variety of methods have been used to prepare N-acyl-aminodiacids. These include the method described in U.S. Pat. No. 3,758,525 to Ajinomoto Co., Inc. There still remains a need, however, for an improved process and, in particular, a process that utilizes non-biohazard solvents and that results in improved yields.

SUMMARY OF THE INVENTION

This invention comprises an improved process of making N-acyl-aminodiacids of Formula I:

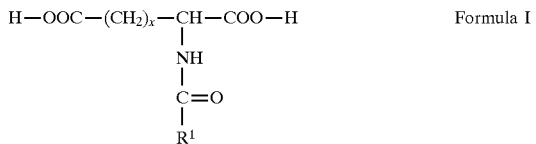

wherein:

$R^1$ is selected from the group consisting of $C_1$–$C_{20}$ alkyl, $C_2$–$C_{20}$ alkenyl, $C_2$–$C_{20}$ alkynyl, wherein the alkenyl and alkynyl groups may contain up to three unsaturations and wherein all of the groups may optionally contain branching; and x=0–10, particularly 1–4.

A particular compound is lauroyl glutamic acid (LGA) where $R^1 = C_{11}$ (n-undecyl group) and x=2.

In the process of the invention an excess of a compound of Formula II:

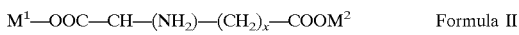

wherein $M^1$ and $M^2$ are each independently selected from the group consisting of hydrogen, sodium, potassium and ammonium, is reacted with a chloride of Formula III:

wherein y=0–18, particularly 7–16, and more particularly is selected from the group consisting of 7, 10, 12, 14 and 16 and mixtures therof.

The reaction in conducted in the presence of a water/alcohol mixture with a sufficient amount of base selected from the group consisting of NaOH, KOH, $Na_2CO_3$ and $K_2CO_3$ (particularly caustic) to form a disalt form of the compound of Formula I. The disalt (such as the disodium salt) is then added to an HCl solution to form the compound of Formula I.

DETAILED DESCRIPTION OF THE INVENTION

This invention relates to an improved method of making compounds of Formula I. First, a compound of Formula II (for example, monosodium glutamate where one of $M^1$ and $M^2$ is sodium, the other of $M^1$ and $M^2$ hydrogen, and x=2) is dissolved in water in a clean vessel equipped with a thermometer, overhead stirrer, pH probe, pressure equalizing funnel containing caustic (for example a 50% solution by weight), pressure equalizing funnel with the acyl chloride selected for the reaction and a subsurface addition tube for the sparging of an inert gas (such as nitrogen). For safety reasons and as needed, the atmosphere of the vessel is then treated to create an atmosphere which is free of oxygen and which will not support combustion. This is done by periodically applying vacuum and purging the vessel with an inert gas such as nitrogen as needed to keep the atmosphere in the vessel in a state where it will not support combustion of an explosive oxygen/solvent mixture in the head space of the vessel.

Next, the vessel is charged with a polar organic solvent selected from the group consisting of (a) $C_1$–$C_6$ alkyl alcohols wherein the alkyl portion may be straight or branched chain; and (b) tetrahydrofuran. Particular solvents of interest are methanol, ethanol, n-propanol, isopropanol, n-butanol, isobutanol, tert-butanol and tetrahydrofuran (THF). Preferred solvents are ethanol, n-propanol and iso-propanol. Standard precautions should be taken with the reaction solvent (such as THF) regarding any potential for flammability. This charging with polar organic solvent may be done by aspirating the solvent into the vessel and is preferrably done without letting air into the vessel as a safety precaution.

After addition of the polar solvent has been completed, the temperature of the reaction vessel is lowered (such as by using a cooling jacket) to a temperature in the range of (−5)–(20) degrees C. and preferably 0–10 degrees (for example, 0 degrees). A nitrogen bleed is then resumed to the vessel to create a positive pressure of the inert gas. Sufficient caustic is added via the funnel described above to maintain the pH in the reaction vessel at a value in the range of 9–13, preferably at a pH of 9–10 initially.

During the time the pH is being adjusted, a chloride of Formula III (for example, lauroyl chloride) is being added to the reaction vessel in an amount such that:

(a) it does not exceed 95% of the molar equivalent amount of the compound of Formula II added initially;

(b) the pH value is maintained in the range of 9–13; and (c) the temperature of the reaction mixture is maintained in the range of 0–10 degrees C. (for example, in the range of 2–10 degrees).

It is preferred that the pH be maintained at a value of about 10 at the outset of the addition of the chloride of Formula III and that the pH be allowed to gradually rise to a value of 12.5–13 during the final stages of the addition of the chloride.

In order to optimize the yield and product quality the temperature of the reaction should be maintained in the range of 0–10 degrees C.; it is preferred that a temperature at the lower end of this range be used, such as 2–5 degrees C. The temperature can be controlled by reactor heat transfer mechanisms, such as with the use of cooling coils or a cooling jacket, and regulating the addition rate of the compound of Formula III. After the charge has been completed, the contents of the reaction vessel are held at a temperature of 2–8 degrees for an additional period of time in the range of 0.5–2 hours (for example, 30 minutes) at a pH greater than or equal to 11, such as a pH of 11–12.

Next the reaction mixture is drowned into a mineral acid. The acid or some dilution of the acid may be added directly to the reaction mixture with later addition of dilution water or the reaction mixture can be poured into an acid solution, provided that in each case sufficient dilution water is included which will equal 5–10 times the volume of the original reaction mixture. Suitable acids include HCl, $H_2SO_4$ and $H_3PO_4$ and especially HCl solution.

One example of a method for accomplishing this drowning step is as follows. In the drowning vessel (now empty) is placed a volume of water which is approximately five times the volume of the reaction mixture with sufficient HCl to obtain a pH value of 1–2. If the volume of the vessel does not permit this, the process may have to be accomplished in portions. The reaction mixture is slowly transferred into the drowning vessel with vigorous mixing. This addition is accomplished at a rate such that the temperature of the mixture remains in the range of 10–70 degrees C. and preferably in the range of 15–20 degrees. HCl is added as needed to keep the pH of the contents of the drowning vessel below 3. Depending on the relative volumes of the reaction and drowning vessels available, it may be necessary to drown the reaction mixture in portions using techniques known to those skilled in the art with periodic filtration as needed. The particle size of the product depends on the temperature, amount of water used, addition rate of the acid chloride, stirring rate and drowning rate. It is preferred that these parameters be adjusted according to the vessel size and reaction conditions so that optimal particle size is obtained for the product. This means that the particle size is large enough to filter well and is preferably uniform in size. If the particle size is too small the filter may become blocked in the next step.

After this step has been completed, complete conversion of the product to the diacid form is effected. Additional acid solution (such as a solution made with HCl) is added to the reaction mixture (all or portions at a time if that is necessary) until the pH of the mixture is below 3, such as in the range of 1.0–1.5. Preferably, the mixture is then heated to a temperature of 60–65 degrees and held at this temperature for a period of 0.25–1 hour (for example, 0.5 hour). The mixture is then cooled to ambient temperature, such as 25 degrees C. (such as with the use of brine, ice water or ethylene glycol in the cooling jacket of the reaction vessel). The mixture is held at ambient temperature until it is filtered to recover the product. It is preferable that the product be filtered promptly to optimize the quality of the product recovered. The filtrate may be disposed of in any acceptable manner.

The press cake from the filtration process is washed with water until the electrical conductivity of the outlet water is approximately the same as the inlet water. This is conveniently done using tap water initially and then switching to deionized water for the final washes. The press cake is squeezed and blown, preferably with nitrogen, to remove more water. The product is dried (for example, on a tray dryer) as required.

It is to be noted that the contact of locally high concentrations of acid chloride and the base (for example, lauroyl chloride and sodium hydroxide) should be carefully avoided by proper location of reagent inlets, configuration of baffles, and design and speed of the stirrer.

EXAMPLES

The following Examples are illustrative of the invention but should not be construed as limitations thereon. Unless otherwise indicated, all chemical symbols, abbreviations and nomenclature have their usual and customary meanings. Percents are in weight percents, temperatures are measured in degrees Centigrade. Unless otherwise specified, the caustic used in the Examples is a 50 percent solution of sodium hydroxide.

Example 1

A reaction vessel of 11,370 liter capacity is charged with monosodium glutamate (1045.5 kg) dissolved in 2464 liters of water. The reaction vessel is purged 3 times with nitrogen at a pressure of 30 psi. Full vacuum is applied to the vessel and suction is used to charge 2462 liters of isopropanol. Care is taken to ensure that no air is allowed to be aspirated during this step. The vacuum is then broken and the vessel is charged with nitrogen to create a nitrogen atmosphere. Using cooling brine in a jacket around the vessel, the temperature of the contents of the reaction vessel is then lowered to a temperature of 0–5 degrees C. A nitrogen bleed is begun to the vessel. Caustic (46.6 liters of 50 percent solution) is added to the reaction vessel to adjust the pH to a value of 10. Lauroyl chloride (1090 kg) is added to the reaction vessel at a rate of 4–5 kg per minute. The pH of the contents of the reaction vessel is maintained in a range of 9–13 at all times using a solution of 50 percent caustic. It is preferred that the pH be maintained at a value of 10 at the outset and that the pH be allowed to gradually rise to a final value of 12–13 during the addition of lauroyl chloride. The temperature of the reaction is maintained between 2–10 degrees C. The temperature is controlled by a reactor heat transfer mechanism and by regulating the addition rate for the lauroyl chloride. After the charge is completed, the contents of the reaction vessel are held at a temperature of 2–8 degrees C. for an additional 30 minutes at a pH of $\geq 11$ (for example, 11–12). A separate reaction vessel is prepared (Vessel B) containing HCl solution. The original reaction vessel (Vessel A) is pressurized with 20–30 psi gauge (psig) nitrogen to transfer its contents to Vessel B and excess nitrogen is vented to the scrubber. Additional water is added to Vessel A in an amount sufficient to remove the product from Vessel A and rinse the contents of Vessel A into Vessel B. The mixture of the contents of Vessel A and the additional water is added to Vessel B in such a manner that the pH is kept below 3.

Alternatively, this last procedure can be done in ¼ increments because of the size of the vessels used. Filtration is done between each ¼ of the material that is processed. In one particular case a total of 7600 gallons (28,769 liters) of water and 3176 pounds (1,185.42 kg.) of 31 percent HCl were used in quater portions.

The reaction mixture which has just been mixed with the HCl solution is adjusted to a pH of 1.0–1.5 with additional HCl. The drowned mixture in Vessel B is heated to a temperature of 60–65 degrees C. and held at this temperature for 30 minutes. The mixture is then cooled to ambient temperature (about 25 degrees C.) using brine in the cooling jacket of the reaction vessel. The mixture is held at this temperature for 90 minutes. The mixture is then filtered, saving the solid and disposing of the filtrate properly. The solid on the filter (also called filter cake or press cake) is washed first with tap water and then with deionized water until the conductivity of the outlet water is approximately the same as that of the inlet water. The press cake is squeezed and blown with nitrogen to remove more water. The product is dried on a tray dryer. Typically the experimental yield using this procedure is 1539–1572 kg (94–96 percent) with a purity of about 96 percent, a melting point of 104–106 degrees C.

What is claimed is:

1. A process for making N-acyl-aminodiacids of Formula I:

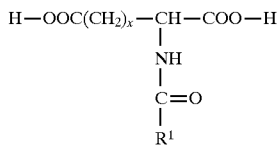 Formula I wherein:

R¹ is selected from the group consisting of $C_1$–$C_{20}$ alkyl, $C_2$–$C_{20}$ alkenyl, and $C_2$–$C_{20}$ alkynyl, wherein the alkenyl and alkynyl groups may contain up to three unsaturations and wherein all of the groups may optionally contain branching; and

X=0–10;

wherein said process comprises (a) a reacting an excess of a compound of Formula II:

 Formula II wherein:

M¹ and M² are each independently selected from the group consisting of hydrogen, sodium, potassium and ammonium with a chloride of Formula III:

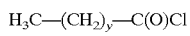 Formula III wherein:

y=0–18, in the presence of a water/solvent mixture with a sufficient amount of base to form a reaction mixture from which a disalt form of the compound of Formula I may be obtained, the solvent mixture including water and an alcohol selected from the group of ethanol, n-propanol, isopropanol; and (b) adding the disalt form of Formula I to an HCl solution to form the compound of Formula I; provided that the compound of Formula III is added in an amount such that:

(a) it does not exceed 95% of the molar equivalent amount of the compound of Formula II added initially;

(b) the pH value of the reaction mixture is maintained in the range of 9–13; and (C) the temperature of the reaction mixture is maintained in the range of 0–10 degrees C.

2. A process as claimed in claim 1 wherein x=1–4.

3. A process as claimed in claim 1 wherein y=7–16.

4. A process as claimed in claim 3 wherein y is selected from the group consisting of 7, 10, 12, 14 and 16 and mixtures thereof.

5. A process as claimed in claim 1 wherein $R^1$=$C_{11}$ and x=2.

6. A process as claimed in claim 1 wherein the compound of Formula II is monosodium glutamate.

* * * * *